US007255878B1

(12) United States Patent
Lahav et al.

(10) Patent No.: US 7,255,878 B1
(45) Date of Patent: Aug. 14, 2007

(54) STABLE BENZIMIDAZOLE FORMULATION

(75) Inventors: Raffael Lahav, deceased, late of Quiriat Bialik (IL); by Erica Lahav, legal representative, Quiriat Bialik (IL); Valerie Azoulay, Pardes Hannah (IL)

(73) Assignee: Dexcel Ltd., Hadera (IL)

( * ) Notice: Subject to any disclaimer, the term of this patent is extended or adjusted under 35 U.S.C. 154(b) by 168 days.

(21) Appl. No.: 10/018,992

(22) PCT Filed: Jun. 21, 2000

(86) PCT No.: PCT/IL00/00364

§ 371 (c)(1), (2), (4) Date: Feb. 19, 2003

(87) PCT Pub. No.: WO00/78284

PCT Pub. Date: Dec. 28, 2000

(30) Foreign Application Priority Data

Jun. 22, 1999 (IL) ..................................... 130602

(51) Int. Cl.
*A61K 9/16* (2006.01)
*A61K 9/00* (2006.01)
*A61K 9/14* (2006.01)
*A61K 9/20* (2006.01)
*A61K 9/22* (2006.01)

(52) U.S. Cl. ...................... 424/490; 424/400; 424/464; 424/465; 424/489; 424/493; 424/494

(58) Field of Classification Search ................ 242/400, 242/464, 489, 490, 493, 494, 485
See application file for complete search history.

(56) References Cited

U.S. PATENT DOCUMENTS 5,817,338 A * 10/1998 Bergstrand et al. ......... 424/468
6,013,281 A * 1/2000 Lundberg et al. ........... 424/468
6,149,942 A * 11/2000 Scheiwe et al. ............ 424/490
6,228,400 B1 * 5/2001 Lee et al. ................... 424/489
6,623,759 B2 * 9/2003 Heese et al. ................ 424/480

FOREIGN PATENT DOCUMENTS

WO WO 99/27917 * 6/1999

* cited by examiner

*Primary Examiner*—Michael G. Hartley
*Assistant Examiner*—Simon J. Oh
(74) *Attorney, Agent, or Firm*—D'vorah Graeser; Dr. D. Graeser Ltd.

(57) ABSTRACT

A stable composition with a benzimidazole derivative, such as Omeprazole, which does not contain a separating layer between the active compound and an enteric coating layer. Instead, the enteric coating layer is applied as a solution with a pH value of at least 6.5, and more preferably in a range of from about 7 to about 10, directly to the benzimidazole derivative substrate. This solution, with the optional addition of a plasticizer, can be directly coated onto the substrate without any necessity for an intermediate layer. Furthermore, in this pH range, the enteric coating is optionally applicable in an aqueous solution, thereby obviating the need for organic solvents for dissolving the enteric coating material. The resultant formulation maintains the stability of the benzimidazole derivative during storage and at the same time protects the product during passage through the acidic environment of the stomach. The problem of interaction between the enteric coat and the alkaline core is thus completely eliminated as the enteric coat at this stage is no longer acidic.

33 Claims, No Drawings

STABLE BENZIMIDAZOLE FORMULATION

FIELD AND BACKGROUND OF THE INVENTION

The present invention relates to a novel stable formulation for an acid labile benzimidazole, and methods of preparation and administration thereof, and in particular, for a stable formulation of a benzimidazole which is suitable for oral administration.

Omeprazole, Pantoprazole, Lansoprazole and other derivatives of benzimidazole, which are active proton pump inhibitors and used conventionally for decreasing gastric secretion are known to be susceptible to degradation and transformation in acid media. Omeprazole, 5-methoxy-2 (((4-methoxy-3,5-dimethyl-2-pyridinyl)methyl)sulfinyl)-1H-benzimidazole, is disclosed and described in European Patent No. 5129 and European Patent No. 124495, as well as in numerous other patents and published patent applications.

The susceptibility of these active proton pump inhibitor substances to degradation and transformation in acid media increases the difficulty of preparing a pharmaceutical form designed for oral administration. If the active substance comes into contact with the stomach content, which is a highly acidic medium, these chemical substances become degraded. Thus, these benzimidazole derivatives should be protected both during storage and during their passage through the acidic environment of the stomach.

The stability of Omeprazole has been extensively studied (see for example A. Pilbrant and C. Cederberg, *Scan. J Gastroenterol.,* 20: 113-120, 1985). Omeprazole degrades with a half-life of less than 10 minutes in an environment with pH values below 4.0. At pH 6.5, the half life of Omeprazole is 18 hours and at pH 11 about 300 days. Therefore, the environment of Omeprazole should be kept at a sufficiently high pH value in order to maintain the stability of the compound, in a formulation which is suitable as a product for oral administration, for example by locating Omeprazole within a core which also contains alkaline constituents. This leads to an alkaline reaction aimed at improving stability of the active substance during manufacture thereof and during storage of the pharmaceutical formulation.

In addition, such a formulation must protect Omeprazole from the acidic environment of the stomach, since if Omeprazole is given orally without any protective coating, it will degrade in the acid environment of the stomach. European Patent No. 237,200 discloses one solution, which is to directly coat the solid core containing Omeprazole, or another benzimidazole derivative, with an enteric coating layer.

However, this apparent solution to the instability of Omeprazole caused further complications, in that the alkaline core containing Omeprazole was found to react with the enteric coating, thereby causing the enteric coating to degrade. A solution to these further complications is disclosed in United Kingdom Patent Application No. 2,189, 698, in which Omeprazole is contained within a solid active core, which is coated first with a subcoating layer and then with an enteric coating layer. The enteric coating layer protects the Omeprazole during the passage through the stomach, while the subcoating layer protects the enteric coating layer from reacting negatively with the alkaline core containing Omeprazole.

The background art describes other attempts to provide formulations which are suitable for oral administration of acid-labile substances. For example, PCT Application No. WO 97/12581 discloses a composition adapted for oral administration containing Omeprazole which specifically does not include alkaline-reacting compounds. Instead, the composition features a core composed of a nuclei and Omeprazole compressed together, an intermediate layer and an enteric layer.

European Patent Application No. 519,144 discloses a formulation for Omeprazole, which features a neutral (sugar) core. Omeprazole is sprayed onto the sugar core, after which an intermediate coating layer and an enteric coating layer are sprayed onto the core.

PCT Application No. WO 98/00114 discloses a modification to other background art formulations for Omeprazole, in which the intermediate subcoating layer is partially neutralized with an alkaline compound. However, this modified formulation still features the subcoating layer, which is a disadvantage in that it complicates the manufacturing process and increases the expense and difficulty of manufacture. Thus, the formulation disclosed in PCT Application No. WO 98/00114, like those disclosed in European Patent Application No. 519,144 and other background art references, has the disadvantage of requiring the intermediate layer.

PCT Application No. WO 83/00435 discloses a solid dosage form, such as a capsule or tablet, containing a pharmacologically active agent coated with an anionic polymer, which is insoluble in gastric juice and in intestinal juice below pH 7. The preferred anionic polymer is a partly methyl esterified methacrylic acid polymer in which the ratio of free carboxylic groups to ester groups is about 1:2. In contrast to the present invention, Omeprazole is not disclosed as one of the active agents.

French Application No. 2,692,146 discloses stable compositions of microgranules of gastro-protected Omeprazole. The composition features a center of Omeprazole diluted in mannitol. This center is coated with an intermediate layer featuring mannitol. An enteric coating is then added over this intermediate layer. PCT Application No. WO 97/12581 discloses a formulation in which an intermediate layer between the core and an enteric coating contains silicium dioxide.

PCT Application No. WO 96/37195 discloses a formulation which lacks a subcoating layer, but which features a core containing titanium dioxide. Both the core containing Omeprazole and the enteric coating layer placed on top of the core include titanium dioxide as an ingredient. Unfortunately, titanium dioxide is only able to mask the discoloration caused by the reaction between Omeprazole and the enteric coating layer, but cannot prevent such an undesirable reaction. Thus, the disclosed formulation does not prevent the undesirable reaction between the benzimidazole derivative and the enteric coating, which is known in the art.

German Patent Application No. 196 26 045 A1 discloses a method for stabilising Omeprazole by coating small tablets or pellets, containing large amounts of mannitol, with a subcoating of Eudragit L. The subcoating of Eudragit L is neutralized, after which a final enteric coat of non-neutralized Eudragit L is applied.

A formulation of a benzimidazole derivative, such as Omeprazole, which lacks an intermediate coating layer and yet which is stable both during storage and during the passage through the stomach, would be highly desirable. Such a formulation would be simpler to manufacture and would expose the sensitive benzimidazole derivative to fewer production steps, thereby decreasing the possibility that the active compound would degrade during production.

Unfortunately, such a stable benzimidazole formulation, which lacks an intermediate layer, is not currently available.

There is thus a unmet need for, and it would be useful to have, a stable benzimidazole formulation, particularly for Omeprazole which lacks an intermediate layer and yet which is stable both during storage and during the passage through the stomach.

SUMMARY OF THE INVENTION

The formulation of the present invention contains a benzimidazole derivative, such as Omeprazole, and is able to maintain the stability of this active ingredient without a separating layer. Instead, the enteric coating layer is applied as a solution with a pH value of at least 6.5, and more preferably in a range of from about 7 to about 10, directly to the benzimidazole derivative substrate. This solution, with the optional addition of a plasticizer, can be directly coated onto the substrate without any necessity for an intermediate layer. Furthermore, in this pH range, the enteric coating is optionally applicable in an aqueous solution, thereby obviating the need for organic solvents for dissolving the enteric coating material.

The resultant formulation maintains the stability of the benzimidazole derivative during storage and at the same time protects the product during passage through the acidic environment of the stomach, where the acidic environment of the stomach causes a partial ionic exchange to occur within the material of the coating. This partial ionic exchange renders the coating impermeable to the acidic liquids of the stomach. On the other hand, during storage the problem of interaction between the enteric coat and the alkaline core is thus completely eliminated as the "enteric coat" is no longer acidic during the storage period.

Preferably, the benzimidazole derivative is selected from the group consisting of Omeprazole, Pantoprazole, Lansoprazole, Leminoprazole, Perprazole, Rabeprazole, and pharmaceutically acceptable salts thereof, as well as any other derivatives of benzimidazole which are proton pump inhibitors and which are conventionally used to decrease gastric secretion.

According to the present invention, there is provided a stable composition for a benzimidazole derivative, the composition comprising: (a) a substrate, the substrate featuring the benzimidazole derivative; and (b) an enteric coating material layered over the substrate, the enteric coating material having a pH value of at least about 6.5.

The substrate can optionally have several different structures. For example, the substrate is optionally an active core containing the benzimidazole derivative, in which the core is a pellet, bead or tablet for example. The active core can be prepared by any conventional method known in the art, including but not limited to, pellets prepared by spheronisation, pellets prepared by coating an inert non pareil seed with Omeprazole, tablets prepared by granulation and compression, as well as any other methods.

The enteric coating material optionally and preferably includes an enteric material selected from the group consisting of hydroxypropyl methylcellulose phthalate, hydroxypropyl methylcellulose acetate succinate, polyvinyl acetate phthalate, cellulose acetate phthalate, cellulose acetate trimellitate, polymethacrylic acid methyl methacrylate and polymethacrylic acid ethyl methacrylate.

More preferably, the enteric coating material further comprises an alkaline compound, such that the pH value is adjusted by adding the alkaline compound to the enteric material. Most preferably, the alkaline compound is an inorganic or organic alkaline salt compound. Even more preferably, the alkaline compound is selected from the group consisting of basic sodium, potassium or ammonium hydroxide. Also most preferably, the pH value is in a range of from about 7 to about 10.

The enteric coating material of the composition could optionally include a plasticizer. Preferably, the plasticizer is selected from the group consisting of a citric acid ester and a phthalic acid ester.

According to another embodiment of the present invention, there is provided a stable composition for a benzimidazole derivative, the composition consisting essentially of: (a) a substrate, the substrate featuring the benzimidazole derivative; and (b) an enteric coating material layered over the substrate, the enteric coating material having a pH value of at least about 6.5.

According to still another embodiment of the present invention, there is provided a method for producing a stable composition for a benzimidazole derivative, the method comprising the steps of: (a) forming a substrate with the benzimidazole derivative; (b) preparing an enteric coating material having a pH value of at least about 6.5; and (c) layering the enteric coating material over the substrate.

DESCRIPTION OF THE PREFERRED EMBODIMENTS

The formulation of the present invention contains a benzimidazole derivative, such as Omeprazole, and is able to maintain the stability of this active ingredient without a separating layer between the active compound and an enteric coating layer. Instead, the enteric coating layer is applied as a solution with a pH value of at least 6.5, and more preferably in a range of from about 7 to about 10, directly to the benzimidazole derivative substrate. This solution, with the addition of a plasticizer, can be directly coated onto the substrate without any necessity for an intermediate layer. Furthermore, in this pH range, the enteric coating is optionally applicable in an aqueous solution, thereby obviating the need for organic solvents for dissolving the enteric coating material.

The resultant formulation maintains the stability of the benzimidazole derivative during storage and at the same time protects the product during passage through the acidic environment of the stomach. The problem of interaction between the enteric coat and the alkaline core is thus completely eliminated as the enteric coat at this stage is no longer acidic.

Without wishing to be limited to a single mechanism, it is hypothesized that as the formulation passes through an acidic environment, such as the acidic environment of the stomach, the outer layer of the enteric coat is converted to an acidic form. This acidic form of the enteric coating material is insoluble in the acidic environment of the stomach. If the formulation is then placed in an environment with a more alkaline pH value, for example by moving into the small intestine, the enteric coat dissolves and releases the active substance.

The use of an enteric coating which includes HPMCP (hydroxypropylmethylcellulose phthalate) neutralized with a basic salt is disclosed in U.S. Pat. No. 5,225,202 and in two scientific articles, "Enteric Film Coating Using Completely Aqueous Dissolved Hydroxypropyl Methyl Cellulose Phthalate Spray Solutions" (J. W. Stafford et al., *Drug Development and Industrial Pharmacy,* 8:513-530, 1982) and "The In Vitro and In Vivo Performance of Aqueous Based Enteric Coats of Neutralized Hydroxypropyl Methyl Cellulose Phthalate" (J. R. Bloor et al., *Drug Development and Industrial Pharmacy,* 15:2227-2243, 1989). However, the disclosed enteric coating is not taught or suggested in any of these references as a suitable direct enteric coating for substrates which contain Omeprazole. As noted previously, Omeprazole and the related benzimidazole derivatives are unusually sensitive molecules, and as such must be carefully protected. Furthermore, U.S. Pat. No. 5,225,202 teaches the necessity for a subcoat between the drug-containing substrate and the enteric coating for drugs which are not compatible with the enteric coating. By contrast, the present invention has been shown to be highly effective without such a subcoat, which is particularly surprising since the background art teaches that formulations containing Omeprazole or another benzimidazole derivative must also feature a subcoat. Neither scientific article even considers the problems associated with acid-sensitive drugs, and as such cannot teach or suggest the formulation of the present invention.

As shown by both the in vitro and in vivo data given below, the formulation of the present invention has been shown to be particularly effective for the oral administration of Omeprazole as the exemplary benzimidazole derivative, a result which could not have been predicted from these references. Indeed, the article by J. R. Bloor et al. teaches away from the use of such a neutralized enteric coating for any formulation, as this article disclosed good in vitro performance of the formulation but poor in vivo performance. By contrast, as described in greater detail below with regard to Example 7, the formulation of the present invention shows good performance in vivo. Thus, the background art neither teaches nor suggests the direct coating of a substrate containing Omeprazole or another benzimidazole derivative with an enteric coating material having a pH value of at least about 6.5, and in fact teaches away from such a formulation.

The preparation of the benzimidazole-containing compositions of the present invention is described first with reference to the following general description and then with reference to the following non-limiting examples of the preparation and application of the compositions of the present invention.

As noted previously, the formulation of the present invention includes a substrate which features the benzimidazole derivative. A solution is prepared with the enteric coating material, which has a pH value of at least 6.5 and more preferably of from about 7 to about 10. Preferably, a pH value in the desired range is obtained by adding an alkaline compound to an enteric coating material. More preferably, the alkaline compound is selected from the group consisting of sodium, potassium or ammonium hydroxide. This enteric coating solution is then layered directly over the substrate to form the composition of the present invention.

The term "substrate" refers to substantially any structure which features the benzimidazole derivative, such as Omeprazole. For example, this structure could be an active core containing the benzimidazole derivative. This active core could be prepared in a number of different ways which are known in the art. For example, the active core could be formed by compressing the benzimidazole derivative with an alkaline substance. As another example, the active core could be prepared by mixing the benzimidazole derivative with an alkaline substance, spheronizing the mixture and then forming cores through pelletisation. As yet another example, the active core is optionally and preferably prepared by embedding the active ingredient in a poloxamer and compressing the embedded material into tablets. The active core is also optionally formed by granulating the active ingredient with an alkaline substance and compressing the granulation into tablets.

Alternatively and optionally, the structure could include a neutral core, such as a sugar bead which does not contain the benzimidazole derivative, over which the benzimidazole derivative is coated. The coating includes Omeprazole or other benzimidazole derivative with a suitable adhesive polymer.

Substantially any type of neutralized suitable enteric coating material could be used in order to coat the benzimidazole substrate, including but not limited to, cellulose acetate phthalate (CAP); hydroxypropyl methylcellulose phthalate (HPMCP); polyvinyl acetate phthalate; cellulose acetate trimellitate; polymethacrylic acid methyl methacrylate or ethyl methacrylate, such as the various types of Eudragit; and hydroxypropyl methylcellulose acetate succinate (HPMCAS). However, preferably the enteric coating material is prepared with the proviso that this material does not contain HPMCP alone, but only in combination with at least one of these 7 other listed enteric coating materials. The particularly preferred enteric coating material is HPMCAS.

As used herein, the term "neutralized enteric coating material" refers to enteric coating material which has been at least partially neutralized by reaction with an alkaline compound, which is preferably a basic inorganic salt. Preferably, the enteric coating material is at least about 60% neutralized, more preferably the enteric coating material is at least about 80% neutralized, and most preferably the enteric coating material is at least about 95% neutralized.

The enteric coating optionally contains a plasticizer, such as a citric acid ester, a phthalic acid ester, or any suitable plasticizer.

The method for applying the enteric coating material to the substrate can vary. Substantially any coating method can be used, such as pan coating or fluidized bed coating, with the solution of the enteric coat chosen. As noted previously, preferably this solution is an aqueous solution. The enteric coating materials described previously can be applied to the substrate in an aqueous solution if the pH value of the solution is adjusted to at least 6.5, and more preferably to an alkaline value, most preferably a pH value from about 7 to about 10.

The following specific examples illustrate various aspects of the compositions of the present invention, and are not intended to be limiting in any way. Specific reference is made to Omeprazole for the purposes of description only and without intending to be limiting.

EXAMPLE 1

This example of the composition of the present invention was prepared as follows. The substrate was in the form of an active core, which was prepared by embedding Omeprazole in poloxamer (Pluronic PE 6800), granulating the resulting mass, adding the necessary auxiliary substances to the mass, and compressing the resultant material into tablets. The substrate was then coated with alkaline polyvinyl acetate phthalate as the enteric coating layer.

| Ingredients | Quantity per tablet |
|---|---|
| Substrate (Active Embedded Core) | |
| Omeprazole | 20 mg |
| Poloxamer (Pluronic PE 6800) | 200 mg |
| Colloidal silicon dioxide | 7 mg |
| Magnesium carbonate | 10 mg |
| Sodium starch glycolate | 12 mg |
| Titanium dioxide | 100 mg |
| Ludipress ® | 226 mg |
| Sodium stearyl fumarate | 25 mg |
| Enteric coating layer | |
| Polyvinyl acetate phthalate | 75 mg |
| Antifoam emulsion | 0.25 mg |
| Sodium hydroxide | 12 mg |

For the preparation of the substrate, the poloxamer was melted at a temperature of 80° C. Omeprazole, together with 2 mg colloidal silicon dioxide, 8 mg of magnesium carbonate, titanium dioxide and 6 mg of sodium starch glycolate were added and mixed thoroughly. Mixing was continued until the melt solidified. The melt was granulated and the rest of the ingredients added to the granulate. The granulate was then compressed into tablets which contained 20 mg Omeprazole. These tablets, which formed the substrate of the composition, were then transferred into a conventional coating pan and coated with the enteric coating layer, prepared in the following manner. First, the antifoam emulsion was dissolved in water to form an aqueous solution. Polyvinyl acetate phthalate was then stirred into this solution for a final concentration of about 10% weight per volume before sodium hydroxide was added. Sodium hydroxide (1 M solution) was then added to adjust the pH value of the solution to about 8, thereby obtaining a basic solution of the enteric coating material. This solution was then sprayed onto the tablets with an incoming air temperature of 40° C.

EXAMPLE 2

This example of the composition of the present invention was prepared as follows. The substrate was prepared by embedding Omeprazole in poloxamer (Pluronic PE 6800) to form tablets, as for Example 1. However, in this Example, the tablets were then coated with hydroxypropyl methylcellulose acetate succinate (HPMCAS) as the enteric coating layer.

| Ingredients | Quantity per tablet |
|---|---|
| Substrate | |
| Omeprazole | 20 mg |
| Poloxamer (Pluronic PE 6800) | 200 mg |
| Colloidal silicon dioxide | 7 mg |
| Sodium starch glycolate | 20 mg |
| Ludipress ® | 228 mg |
| Sodium stearyl fumarate | 25 mg |
| Enteric coating layer | |
| Hydroxypropyl Methylcellulose Acetate Succinate (HPMCAS) | 43 mg |
| Triethyl citrate | 12 mg |
| Sodium lauryl sulfate | 1.3 mg |
| Talc | 21.4 mg |
| Sodium hydroxide | 2.3 mg |

The tablets were prepared as for Example 1, except that titanium dioxide was omitted. The tablets were then coated in a conventional coating pan with the enteric coating solution, which was prepared as follows. First, triethyl citrate was dissolved in water to form an aqueous solution. Sodium lauryl sulfate was then added to this aqueous solution. The HPMCAS and talc were dispersed in this solution, such that the concentration of HPMCAS was about 10% weight per volume. Sodium hydroxide (1M solution) was then added to adjust the pH value of the solution to a value from about 7 to about 10. The enteric coating was layered over the substrate by spraying the solution with an incoming air temperature of 40° C.

EXAMPLE 3

This example of the composition of the present invention was prepared as for Example 1, except that the enteric coating contained alkaline HPMCP (hydroxypropylmethylcellulose phthalate) rather than HPMCAS.

| Ingredients | Quantity per tablet |
|---|---|
| Substrate | |
| Omeprazole | 20 mg |
| Poloxamer (Pluronic PE 6800) | 200 mg |
| Colloidal silicon dioxide | 7 mg |
| Sodium starch glycolate | 10 mg |
| Titanium dioxide | 83 mg |
| Ludipress ® | 145 mg |
| Sodium stearyl fumarate | 25 mg |
| Enteric coating layer | |
| HPMC Phthalate (HP-55) | 56.2 mg |
| Triethyl citrate | 22.5 mg |
| Sodium hydroxide | 9 mg |

The substrate was prepared as described in Example 1, and was then coated in a conventional coating pan with the enteric coating solution by spraying the solution at an incoming air temperature of 40° C. The enteric coating solution was prepared as follows. The HPMC phthalate was suspended in the water to a concentration of about 10% weight per volume (before sodium hydroxide was added). Sodium hydroxide (1M solution) was then added to this aqueous suspension until the HPMCP dissolved. The resultant solution has a pH value in a range of from about 8 to about 10. The triethyl citrate was then added to the resultant solution in order to form the enteric coating solution, which was then layered over the substrate as previously described.

EXAMPLE 4

In this example of the composition of the present invention, the substrate has two parts: a neutral core; and a coating layer containing the active ingredient, which was layered over the neutral core. The substrate was then coated with the enteric coating solution. Hard gelatin capsules were then filled with the resultant pellets.

| Substrate | |
| --- | --- |
| Neutral core | Quantity per capsule |
| Sugar spheres 20/25 (700-850 microns) | 161.63 mg |

| Ingredients | Quantity per capsule |
| --- | --- |
| Active coating | |
| Omeprazole | 20.00 mg |
| Hydroxypropyl methylcellulose 2910 | 5.33 mg |
| Hydroxypropyl cellulose | 6.00 mg |
| Lactose | 8.00 mg |
| Disodium phosphate anhydrous | 0.64 mg |
| Sodium lauryl sulfate | 0.50 mg |
| Enteric coating layer | |
| HPMCAS | 21.00 mg |
| Triethyl citrate | 6.00 mg |
| Sodium lauryl sulfate | 0.66 mg |
| Talc | 11.00 mg |
| Sodium hydroxide | 1.12 mg |

The composition of the present invention was prepared according to this Example as follows. First, sugar spheres were placed in a fluid bed coating chamber, equipped with a Wurster bottom spraying device. A suspension of the ingredients in water was then prepared so that the concentration was approximately 20% of total solids in water. This active coating suspension was sprayed onto the sugar spheres. A suspension of the enteric coating was prepared according to Example 2. This enteric coating was then sprayed onto the substrate in order to form the finished pellets. The pellets were then placed in capsules.

EXAMPLE 5

This example of the composition of the present invention was prepared with a compressed tablet as the substrate. The tablet was then coated with alkaline HPMCAS (Hydroxypropyl Methylcellulose Acetate Succinate) as the enteric coating layer, preferably having a pH in a range of from about 7 to about 10.

| Ingredients | Quantity per tablet |
| --- | --- |
| Substrate (Active Compressed Tablet Core) | |
| Omeprazole | 20 mg |
| Lactose | 192.5 mg |
| Magnesium carbonate | 10 mg |
| Sodium starch glycolate | 10 mg |
| Povidone | 10 mg |
| Sodium stearyl fumarate | 7.5 mg |
| Enteric coating layer | |
| HPMCAS | 16.1 mg |
| Triethyl citrate | 4.5 mg |
| Sodium lauryl sulfate | 0.5 mg |
| Talc | 8.04 |
| Sodium hydroxide | 0.86 mg |

For the preparation of the substrate, Omeprazole, together with lactose, magnesium carbonate, sodium starch glycolate, and povidone were mixed thoroughly. The mixture was then granulated with a sufficient quantity of water, and dried. Sodium stearyl fumarate was then added to the mixture, which was then compressed into tablets weighing 250 mg each.

These tablets, which formed the substrate of the composition, were then transferred into a conventional coating pan and coated with the enteric coating layer, prepared as described in Example 4.

EXAMPLE 6

Stability tests were performed with formulations prepared according to Examples 2 and 3. For the first test, both coated and uncoated tablets prepared according to either Example 2 or Example 3 were placed into a box which was open to the environment. The open box was then stored at 40° C. and 75% relative humidity, which are very stringent conditions. The coated and uncoated tablets were examined initially, after a week and after a month to determine stability. The results are shown in the tables below.

Tablets Prepared According to Example 2

| Sampled Material | Appearance of Sample | | |
| --- | --- | --- | --- |
| | Initial | After One Week | After One Month |
| coated tablet | off white | deeper off white | deeper off white |
| uncoated tablet | white | white | white |

Tablets Prepared According to Example 3

| Sampled Material | Appearance of Sample | | |
| --- | --- | --- | --- |
| | Initial | After One Week | After One Month |
| coated tablet | off white | off white | deeper off white |
| uncoated tablet | white | white | white |

The term "deeper off white" refers to a more intense off white color which was observed for some samples, as described in greater detail above. These results show that coated tablets prepared according to either Example 2 or Example 3 showed good stability, even after one month of storage under particularly stringent conditions.

In a second stability test, coated tablets were prepared according to Example 2. These coated tablets were then packed into an Alu/Alu (Aluminum/Aluminum) blister, which is a well known technique in the art for packing certain oral dosage forms. The blister was then stored under accelerated conditions of 30° C. and 60% relative humidity; or 40° C. and 75% relative humidity. Samples of the tablets were examined initially, and after one month of storage under one of these conditions. In addition, samples were assayed to determine the amount of Omeprazole present in the coated tablet, as listed under "Assay" as milligrams of Omeprazole per tablet. A dissolution test was performed, using the accepted USP method. The coated tablets were placed in 0.1 N HCl for 2 hours, followed by a solution at pH 6.8 with stirring with a paddle at 100 rpm for 15 minutes, 30 minutes or 45 minutes. Gastric resistance was also examined by placing the coated tablets in a simulated gastric fluid for 2 hours (pH of approximately 1), as is well known in the art. The results are shown in the table below.

| | Time (min) | Initial | 30° 60% RH | 40° 75% RH |
|---|---|---|---|---|
| Description | NA | Off white | Off white | Off white |
| Assay | NA | 20.4 mg | 19.39 mg | 19.66 mg |
| Dissolution | 120 | 0% | 0% | 0% |
| | 135 | 52% | 42% | 39% |
| | 150 | 96% | 85% | 90% |
| | 165 | 105% | 99% | 104% |
| Gastric Resistance | NA | 101% | 98% | 96% |

These results show that the coated tablets, prepared according to Example 2, show good stability and gastric resistance, yet are also able to dissolve in an appropriate time-dependent manner.

EXAMPLE 7

A one-way pharmacokinetic pilot study was performed in vivo for testing the pharmacokinetic profile of the coated tablets, which were prepared according to Example 2. The study was performed with ten healthy male volunteers, who received a single dosage of the coated tablets, containing 20 mg of Omeprazole. The results showed that Omeprazole administered in the coated tablets of the present invention had a similar lag time to absorption in comparison to a previous study performed with the reference product, which is the 20 mg Omeprazole dosage form of the formulation of Astra (Aktiebolaget Hassle), and also as described in the literature (see for example Duvauchelle, T. et al., "Comparative Bioavailability Study of Two Oral Omeprazole Formulations After Single and Repeated Administrations in Healthy Volunteers", *Pharmacokinetics,* 16: 141-149, 1998). The lag time to absorption is defined as the time between the administration of the formulation and the first detection of the active ingredient in the samples taken from the subject, according to the sampling method employed.

In addition, comparable bioavailability was achieved with the coated tablets of the present invention, both to values obtained in the previous study with the reference product and to values which were described in the literature (see for example the previously referenced article in *Pharmacokinetics*). Furthermore, the values obtained for Cmax and Tmax concerning the rate of absorption were comparable to results obtained in the previous study performed with the reference product, and as described in the literature (see for example the previously referenced article in *Pharmacokinetics*). Thus, the coated tablets of the present invention clearly show good performance both in vitro, as described in Example 6, and in vivo.

EXAMPLE 8

Coated pellets were prepared according to the process previously described above in Example 4. However, the pellets were coated with the following suspension:

| Enteric coating (quantities per capsule) | |
|---|---|
| HPMCAS | 21.00 mg |
| Triethyl Citrate | 6.00 mg |
| Sodium lauryl sulfate | 0.66 mg |
| Colloidal silicon dioxide | 2.10 mg |
| Sodium hydroxide | 1.12 mg |

EXAMPLE 9

Although the previous Examples used aqueous solutions for providing an optimal coating, the possibility of increasing the concentration of the enteric coating polymer by using an alcohol-based solution was studied in this Example.

Coated pellets were prepared according to the process of Example 4, except that these pellets were coated with the following solution, to obtain the required protection in an acidic environment.

| | Enteric coating | |
|---|---|---|
| | Solution prepared | Quantities per capsule |
| Alcohol 95% | 1.900 kg | N/A |
| Water | 0.830 kg | N/A |
| HPMCAS | 0.476 kg | 21.00 mg |
| Triethyl citrate | 0.136 kg | 6.00 mg |
| Sodium lauryl sulfate | 0.015 kg | 0.66 mg |
| Colloidal silicon dioxide | 0.047 kg | 2.1 mg |
| Sodium hydroxide | 0.025 kg | 1.12 mg |

EXAMPLE 10

| Substrate (Active Compressed Tablet Core) | |
|---|---|
| Ingredients | Quantity per tablet |
| Omeprazole | 20 mg |
| Lactose | 203 mg |
| Magnesium carbonate | 10 mg |
| Sodium starch glycolate | 10 mg |
| Sodium stearyl fumarate | 7 mg |

| Enteric coating layer | |
|---|---|
| Ingredients | Quantity per tablet |
| HPMCAS | 16 mg |
| Triethyl citrate | 4.5 mg |
| Sodium lauryl sulfate | 0.5 mg |
| Talc | 8.14 mg |
| Sodium hydroxide | 0.86 mg |
| Sepisperse ™ (pink pigment) | 10.8 mg |

For the preparation of the substrate, Omeprazole was mixed together thoroughly with lactose, sodium starch glycolate, magnesium carbonate and sodium stearyl fumarate. The mixture was then compressed into tablets weighing 250 mg each. These tablets were then transferred into a conventional coating pan and coated with the enteric coating layer, prepared as described in Example 4, with the addition of a pigment to the enteric coating material.

EXAMPLE 11

Stability tests were performed with the formulation prepared according to Example 10. For the tests, the tablets were packed into alu-alu blister. The blister was then stored under room temperature or under accelerated conditions of 30° C. and 60% relative humidity (RH), or 40° C. and 75% relative humidity. Samples of the tablets were examined initially and after 6 months of storage under one of these conditions. In addition samples were assayed. A dissolution test was performed, and gastric resistance was also examined. The tablet gave good stability results even after storage at 40° C. The results are shown in the table below.

| Test performed | Initial | 25° C. 6 month | 30° C./60% RH 6 month | 40° C./75% RH 6 month |
|---|---|---|---|---|
| Visual Description | conform | conform | conform | conform |
| Assay | 19.76 mg per tablet | 20.19 mg per tablet | 19.97 mg per tablet | 19.28 mg per tablet |
| Dissolution | 96% | 96% | 96% | 96% |
| Gastric Resistance | 96% | 96% | 95% | 94% |

EXAMPLE 12

A two-way pharmacokinetic study was performed in vivo for testing the bioequivalence of the coated tablets which were prepared according to Example 10, as compared to the reference product which is the 20 mg Omeprazole dosage form of the formulation of Astra (Sweden), called Losec™. The study was performed on 39 volunteers. As shown in the table below, the results of the study showed that the two products exhibited very similar pharmacokinetic profiles, such that the two formulations can be considered to be bioequivalent.

| Formulation | AUC (ng × hour/ml) | Cmax (ng/ml) | Tmax (hours) |
|---|---|---|---|
| Formulation of the present invention (Example 10) | 426 ± 256 | 217 ± 109 | 1.08 ± 0.64 |
| Losec ™ (Astra) | 434 ± 226 | 246 ± 113 | 1.56 ± 0.79 |

EXAMPLE 13

| Substrate (Active Compressed Tablet Core) | |
|---|---|
| Ingredients | Quantity per tablet |
| Omeprazole | 20 mg |
| Lactose | 203 mg |
| Sodium hydrogen carbonate | 10 mg |
| Sodium starch glycolate | 10 mg |
| Sodium stearyl fumarate | 7 mg |

| Enteric coating layer | |
|---|---|
| Ingredients | Quantity per tablet |
| HPMCAS | 16 mg |
| Triethyl citrate | 4.5 mg |
| Sodium lauryl sulfate | 0.5 mg |
| Talc | 8.14 mg |
| Sodium hydroxide | 0.86 mg |
| Sepisperse ™ | 10.8 mg |

For the preparation of the substrate, Omeprazole was thoroughly mixed together with lactose, sodium starch glycolate, sodium hydrogen carbonate and sodium stearyl fumarate. The mixture was then compressed into tablets weighing 250 mg each. These tablets were then transferred into a conventional coating pan and coated with the enteric coating layer, prepared as described in Example 4.

EXAMPLE 14

| Substrate (Active Compressed Tablet Core) | |
|---|---|
| Ingredients | Quantity per tablet |
| Omeprazole | 20 mg |
| Lactose | 203 mg |
| Trisodium citrate | 10 mg |
| Sodium starch glycolate | 10 mg |
| Sodium stearyl fumarate | 7 mg |

| Enteric coating layer | |
|---|---|
| Ingredients | Quantity per tablet |
| HPMCAS | 16 mg |
| Triethyl citrate | 4.5 mg |
| Sodium lauryl sulfate | 0.5 mg |
| Talc | 8.14 mg |
| Sodium hydroxide | 0.86 mg |
| Sepisperse ™ | 10.8 mg |

For the preparation of the substrate, Omeprazole was mixed thoroughly together with lactose, sodium starch glycolate, trisodium citrate and sodium stearyl fumarate. The mixture was then compressed into tablets weighing 250 mg each. These tablets were then transferred into a conventional coating pan and coated with the enteric coating layer, prepared as described in Example 4.

EXAMPLE 15

Stability tests were performed with the formulations prepared according to Examples 10, 13 and 14. Both coated and non-coated tablets were placed into an open box and stored at 40° C. and 75% relative humidity, which are very stringent conditions. The coated and uncoated tablets were examined initially after 1 week and again after 2 weeks to determine stability. The results are shown in the tables below.

Tablets prepared according to Example 10

| Sampled material | Appearance of sample Initial | After 1 week | After 2 weeks |
|---|---|---|---|
| Coated | Pink | Pink | Pink |
| Uncoated | White | White | White |

Tablets prepared according to Example 13

| Sampled material | Appearance of sample Initial | After 1 week | After 2 weeks |
|---|---|---|---|
| Coated | Pink | Pink | Pink |
| Uncoated | White | White | White |

Tablets prepared according to Example 14

| Sampled material | Appearance of sample Initial | After 1 week | After 2 weeks |
|---|---|---|---|
| Coated | Pink | Pink | Pink |
| Uncoated | White | White | White |

While the invention has been described with respect to a limited number of embodiments, it will be appreciated that many variations, modifications and other applications of the invention may be made.

What is claimed is:

1. A method for producing a stable tablet composition for a benzimidazole derivative, the method consisting essentially of:

forming a substrate with the benzimidazole derivative;

preparing a solution of an enteric polymer selected from the group consisting of HPMCAS, CAP, polyvinyl acetate phthalate, cellulose acetate trimellitate, polymethacrylic acid methacrylate, and ethyl methacrylate;

neutralizing said solution by addition of an alkalizing material comprising a material selected from the group consisting of an inorganic or organic alkaline compound; and applying a single layer of said neutralized solution directly to said substrate, without an intermediate layer between said substrate and said enteric coating.

2. The method of claim 1, wherein said neutralized solution is at least about 60% neutralized.

3. The method of claim 2, wherein said neutralized solution is at least about 80% neutralized.

4. The method of claim 3, wherein said neutralized solution is at least about 95% neutralized.

5. The method of claim 1, wherein said substrate is formed by melting poloxamer and by mixing the benzimidazole derivative into said poloxamer.

6. The method of claim 1, wherein said substrate is formed by direct compression.

7. The method of claim 1, wherein said substrate is formed by wet granulation.

8. The method of claim 1, wherein said substrate is formed by coating on an inert core.

9. The method of claim 1, wherein said coating comprises spraying.

10. The method of claim 1, wherein said applying said neutralized solution comprises spraying said solution with an incoming air temperature of at least 40° C.

11. The method of claim 1, wherein said applying said neutralized solution comprises a method selected from the group consisting of pan coating and fluidized bed coating.

12. A method for producing a stable tablet composition for a benzimidazole derivative, the method consisting essentially of:

forming a substrate with the benzimidazole derivative;

preparing an aqueous solution of an enteric polymer selected from the group consisting of HPMCAS, CAP, polyvinyl acetate phthalate, cellulose acetate trimellitate, polymethacrylic acid methacrylate, and ethyl methacrylate;

neutralizing said solution by addition of an alkalizing material comprising a material selected from the group consisting of sodium, potassium or ammonium hydroxide;

spraying a single layer of said neutralized solution directly over said substrate, without an intermediate layer between said substrate and said enteric coating.

13. The method of claim 12, wherein said neutralized solution is at least about 60% neutralized.

14. The method of claim 13, wherein said neutralized solution is at least about 80% neutralized.

15. The method of claim 14, wherein said neutralized solution is at least about 95% neutralized.

16. The method of claim 12, wherein said substrate is formed by melting poloxamer and by mixing the benzimidazole derivative into said poloxamer.

17. The method of claim 12, wherein said substrate is formed by direct compression.

18. The method of claim 12, wherein said substrate is formed by wet granulation.

19. The method of claim 12, wherein said substrate is formed by coating on an inert core.

20. The method of claim 12, wherein said coating comprises spraying.

21. The method of claim 12, wherein said applying said neutralized solution comprises spraying said solution with an incoming air temperature of at least 40° C.

22. The method of claim 12, wherein said applying said neutralized solution comprises a method selected from the group consisting of pan coating and fluidized bed coating.

23. A method for producing a stable tablet composition for a benzimidazole derivative, the method consisting essentially of;

forming a substrate with the benzimidazole derivative;

preparing an aqueous solution of an enteric polymer selected from the group consisting of HPMCAS, CAP, polyvinyl acetate phthalate, cellulose acetate trimellitate, polymethacrylic acid methacrylate, and ethyl methacrylate;

neutralizing said solution by addition of an alkalizing material comprising at least ammonium hydroxide;

adding a plasticizer to said solution before or after said neutralizing; and directly coating said substrate with a single layer of said neutralized solution, without an intermediate layer between said substrate and said enteric coating.

24. The method of claim 23, wherein said neutralized solution is at least about 60% neutralized.

25. The method of claim 23, wherein said neutralized solution is at least about 80% neutralized.

26. The method of claim 25, wherein said neutralized solution is at least about 95% neutralized.

27. The method of claim 23, wherein said substrate is formed by melting poloxamer and by mixing the benzimidazole derivative into said poloxamer.

28. The method of claim 23, wherein said substrate is formed by direct compression.

29. The method of claim 23, wherein said substrate is formed by wet granulation.

30. The method of claim 23, wherein said substrate is formed by coating on an inert core.

31. The method of claim 23, wherein said coating comprises spraying.

32. The method of claim 23, wherein said applying said neutralized solution comprises spraying said solution with an incoming air temperature of at least 40° C.

33. The method of claim 23, wherein said applying said neutralized solution comprises a method selected from the group consisting of pan coating and fluidized bed coating.

* * * * *